United States Patent [19]

Diehr et al.

[11] Patent Number: 4,725,304

[45] Date of Patent: * Feb. 16, 1988

[54] FLUOROALKOXYPHENYLSULPHONYL-GUANIDINES

[75] Inventors: Hans-Joachim Diehr; Christa Fest, both of Wuppertal; Rolf Kirsten, Monheim; Joachim Kluth, Langenfeld; Klaus-Helmut Müller, Duesseldorf; Theodor Pfister, Monheim; Uwe Priesnitz, Solingen; Hans-Jochem Riebel, Wuppertal; Wolfgang Roy, Langenfeld; Hans-Joachim Santel, Cologne; Robert R. Schmidt, Bergisch-Gladbach, all of Fed. Rep. of Germany

[73] Assignee: Bayer Aktiengesellschaft, Leverkusen, Fed. Rep. of Germany

[*] Notice: The portion of the term of this patent subsequent to Jul. 29, 2003 has been disclaimed.

[21] Appl. No.: 769,182

[22] Filed: Aug. 23, 1985

[30] Foreign Application Priority Data

Aug. 30, 1984 [DE] Fed. Rep. of Germany ....... 3431916

[51] Int. Cl.$^4$ .................. C07D 239/69; C07D 239/42; A01N 43/54
[52] U.S. Cl. ........................................ 71/92; 544/122; 544/330
[58] Field of Search ..................... 71/92; 544/122, 330

[56] References Cited

U.S. PATENT DOCUMENTS 4,602,938 7/1986 Moriya et al. ....................... 544/332

FOREIGN PATENT DOCUMENTS 0117014 8/1984 European Pat. Off. .
0148498 7/1985 European Pat. Off. .
1089210 6/1959 Fed. Rep. of Germany .
71016 1/1970 Fed. Rep. of Germany .
84530 9/1971 Fed. Rep. of Germany .
3334455 9/1984 Fed. Rep. of Germany .

Primary Examiner—John M. Ford
Attorney, Agent, or Firm—Sprung Horn Kramer & Woods

[57] ABSTRACT

Novel herbicidally active fluoroalkoxyphenylsulphonylguanidines of the formula

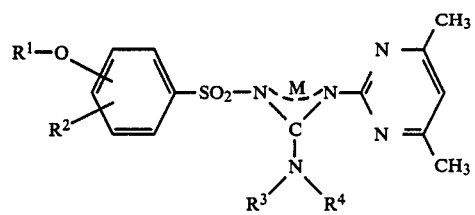

in which
M is hydrogen or one equivalent of a metal,
$R^1$ is fluorine-substituted alkyl, and
$R^2$, $R^3$ and $R^4$ each independently is hydrogen or various organic radicals,
or 1:1 adducts thereof with strong acids.

8 Claims, No Drawings

FLUOROALKOXYPHENYLSULPHONYLGUANIDINES

The invention relates to new fluoroalkoxyphenylsulphonylguanidines, processes for their preparation and their use as herbicides.

Various guanidine derivatives have been disclosed as potential herbicides in patent specifications (compare DE-AS (German Published Specification) No. 1,089,210 and East German Patent Specification Nos. 71,016 and 84,530), but have not yet achieved greater importance as agents for combating weeds and/or regulating plant growth. Other guanidine derivatives are disclosed in application Ser. No. 578,345, filed Feb. 9, 1984, now pending, corresponding to DE-OS (German Published Specification) No. 3,334,455 (see also EP-A No. 117,014) as well as in copending commonly assigned applications.

New fluoroalkoxyphenylsulphonylguanidines of the general formula (I)

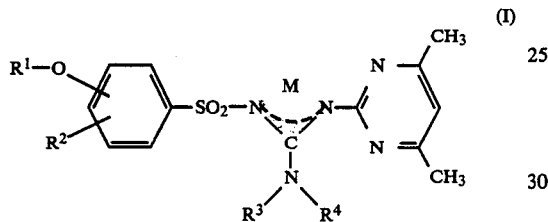

in which
M represents hydrogen or one equivalent of a metal,
$R^1$ represents $C_1$-$C_4$-alkyl, which contains at least one fluorine substituent and optionally also one or more chlorine substituents,
$R^2$ represents hydrogen or halogen,
$R^3$ represents hydrogen, $C_1$-$C_6$-alkyl [which is optionally substituted by fluorine, chlorine, bromine, cyano, hydroxyl or $C_1$-$C_4$-alkoxy], $C_3$-$C_6$-cycloalkyl, $C_3$-$C_6$-alkenyl, $C_3$-$C_6$-alkinyl, benzyl [which is optionally substituted by fluorine, chlorine, nitro, cyano, $C_1$-$C_4$-alkyl, $C_1$-$C_4$-alkoxy or $C_1$-$C_4$-alkoxycarbonyl] or the radical

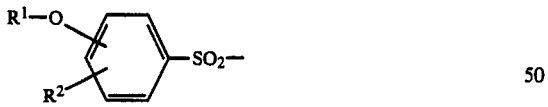

wherein
$R^1$ and $R^2$ have the abovementioned meanings; and in which, furthermore,
$R^4$ represents hydrogen, $C_1$-$C_6$-alkyl [which is optionally substituted by fluorine, chlorine, bromine, cyano, carboxyl, $C_1$-$C_4$-alkoxycarbonyl, hydroxyl or $C_1$-$C_4$-alkoxy], $C_3$-$C_6$-cycloalkyl, $C_3$-$C_6$-alkenyl, $C_3$-$C_6$-alkinyl, phenethyl or benzyl [which is optionally substituted by fluorine, chlorine, nitro, cyano, $C_1$-$C_4$-alkyl, $C_1$-$C_4$-alkoxy or $C_1$-$C_4$-alkoxy-carbonyl] or phenyl [which is optionally substituted by fluorine, chlorine, bromine, hydroxyl, cyano, nitro, amino, $C_1$-$C_4$-alkyl, trifluoromethyl, $C_1$-$C_4$-alkoxy, trifluoromethoxy, $C_1$-$C_4$-alkylthio, trifluoromethylthio, aminosulphonyl or $C_1$-$C_4$-alkoxy-carbonyl], or $R^3$ and $R^4$ together represent $C_4$-$C_6$-alkanediyl, which is optionally interrupted by an oxygen bridge or by a bridge

wherein
$R^5$ represents $C_1$-$C_4$-alkyl, $C_1$-$C_4$-alkylcarbonyl or phenyl [which is optionally substituted by fluorine, chlorine, bromine, cyano, nitro, $C_1$-$C_4$-alkyl, trifluoromethyl or $C_1$-$C_4$-alkoxy];
or in which, furthermore,
$R^4$ represents the radical —O—$R^6$
wherein
$R^6$ represents $C_1$-$C_8$-alkyl [which is optionally substituted by fluorine, chlorine, $C_1$-$C_4$-alkoxy, $C_1$-$C_4$-alkylthio, $C_1$-$C_4$-alkylsulphinyl or $C_1$-$C_4$-alkylsulphonyl], $C_3$-$C_6$-alkenyl, $C_1$-$C_4$-alkoxy-carbonyl-$C_1$-$C_2$-alkyl, aminocarbonylmethyl, $C_1$-$C_4$-alkylamino-carbonyl-methyl, di($C_1$-$C_4$-alkyl)-amino-carbonyl-methyl; phenyl, phenethyl or benzyl [which are optionally substituted by fluorine, chlorine, nitro, cyano, $C_1$-$C_4$-alkyl, $C_1$-$C_4$-alkoxy or $C_1$-$C_4$-alkoxy-carbonyl], $C_3$-$C_6$-cycloalkyl or $C_3$-$C_6$-cycloalkyl-$C_1$-$C_4$-alkyl;
or in which, furthermore,
$R^4$ represents the radical

wherein
$R^7$ represents hydrogen or $C_1$-$C_4$-alkyl and
$R^8$ represents $C_1$-$C_4$-alkyl [which is optionally substituted by fluorine, chlorine, bromine, cyano, $C_1$-$C_4$-alkoxy or $C_1$-$C_4$-alkoxy-carbonyl], $C_3$-$C_6$-cycloalkyl, phenethyl, benzyl or phenyl [which are optionally substituted by fluorine, chlorine, bromine, nitro, cyano, $C_1$-$C_4$-alkyl, $C_1$-$C_4$-alkoxy or $C_1$-$C_4$-alkoxy-carbonyl], and 1:1 adducts of compounds of the formula (I) with strong acids, have now been found.

If M represents hydrogen, the general formula (I) represents the individual tautomers of the formula (IA) and (IB)

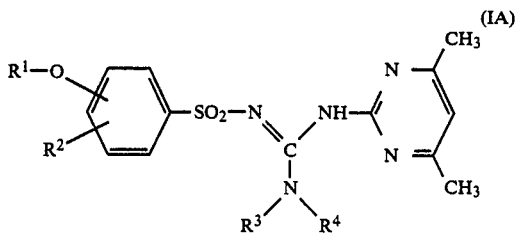

-continued

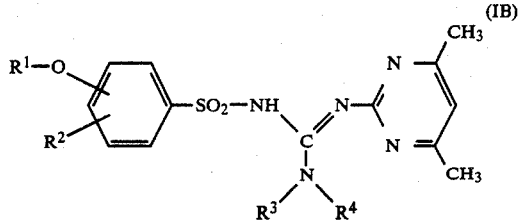
(IB)

in which
R$^1$, R$^2$, R$^3$ and R$^4$ have the abovementioned meaning, and mixtures of the tautomers (IA) and (IB).

The ratio of (IA)/(IB) in the mixture depends on factors which determine the state of aggregation, such as, for example, the temperature, solvent and concentration.

In the case where, besides M, R$^3$ also represents hydrogen, another tautomeric form (IC) is possible:

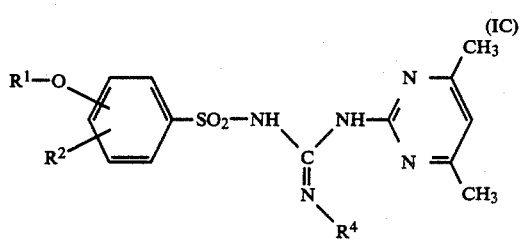
(IC)

All these tautomers are claimed in the context of the present invention.

The new fluoroalkoxyphenylsulphonylguanidines of the formula (I) are obtained (a) for the case where M represents hydrogen and R$^3$ represents the radical

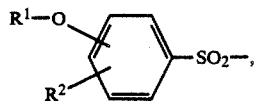

by a process in which guanidine derivatives of the formula (II)

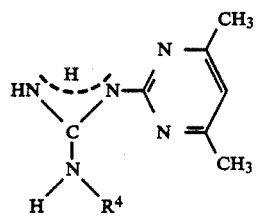
(II)

in which
R$^4$ has the abovementioned meaning,
are reacted with at least two molar equivalents of fluoroalkoxybenzenesulphonic acid chlorides of the formula (III)

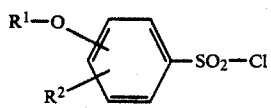
(III)

in which
R$^1$ and R$^2$ have the abovementioned meanings, in the presence of acid acceptors and if appropriate in the presence of diluents; or (b) in the case where M represents hydrogen and R$^3$ represents hydrogen, C$_1$–C$_6$-alkyl [which is optionally substituted as mentioned above], C$_3$–C$_6$-cycloalkyl, C$_3$–C$_6$-alkenyl or benzyl [which is optionally substituted as mentioned above], or, together with R$^4$, has the abovementioned meaning, by a process in which the fluoroalkoxyphenylsulphonylguanidines obtainable by the process described under (a), of the formula (ID)

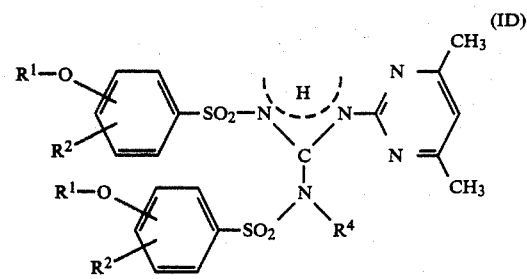
(ID)

in which
R$^1$, R$^2$ and R$^4$ have the abovementioned meaning, are reacted with amino compounds of the formula (IV)

(IV)

in which
R$^3$ has the meaning given above under (b) and
R$^4$ has the abovementioned meaning,
or with hydrochlorides of amino compounds of the formula (IV), if appropriate in the presence of acid acceptors and if appropriate in the presence of diluents; or (c) in the case where M represents one equivalent of a metal, by a process in which the compounds obtainable by the processes described above under (a) and (b), of the formula (I), in which M represents hydrogen and R$^1$, R$^2$, R$^3$ and R$^4$ have the abovementioned meaning, are reacted with metal hydroxides, hydrides or alkanolates or with organometallic compounds, if appropriate in the presence of diluents; or (d) in the case where 1:1 adducts of compounds of the formula (I) with strong acids are to be prepared, by a process in which compounds of the formula (I) in which M represents hydrogen and R$^1$, R$^2$, R$^3$ and R$^4$ have the abovementioned meanings, are reacted with strong acids, if appropriate in the presence of diluents.

The new fluoroalkoxyphenylsulphonylguanidines of the formula (I) and their adducts with strong acids are distinguished by a powerful herbicidal activity.

Surprisingly, the new compounds of the formula (I) exhibit a considerably better herbicidal action than the previously known guanidines of the same type of action.

The invention preferably relates to compounds of for formula (I) in which
M represents hydrogen or one equivalent of sodium, potassium or calcium, $R^1$ represents $C_1-C_2$-alkyl, which contains at least two fluorine substituents and optionally also one chlorine substituent, $R^2$ represents hydrogen or chlorine, $R^3$ represents hydrogen, $C_1-C_4$-alkyl [which is optionally substituted by fluorine, chlorine, bromine, cyano, hydroxyl or $C_1-C_2$-alkoxy], $C_3-C_6$-cycloalkyl, $C_3-C_6$-alkenyl, $C_3-C_6$-alkinyl, benzyl or the radical

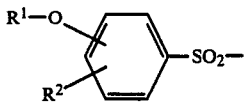

wherein $R^1$ and $R^2$ have the abovementioned meanings; and in which, furthermore, $R^4$ represents hydrogen, $C_1-C_4$-alkyl [which is optionally substituted by fluorine, chlorine, bromine, cyano, carboxyl, $C_1-C_3$-alkoxycarbonyl, hydroxyl or $C_1-C_2$-alkoxy], $C_3-C_6$-cycloalkyl, $C_3-C_6$-alkenyl, $C_3-C_6$-alkinyl, phenethyl or benzyl [which is optionally substituted by fluorine, chlorine, nitro, cyano, $C_1-C_2$-alkyl, $C_1-C_2$-alkoxy or $C_1-C_2$-alkoxycarbonyl] or phenyl [which is optionally substituted by fluorine, chlorine, bromine, hydroxyl, cyano, nitro, amino, $C_1-C_4$-alkyl, trifluoromethyl, $C_1-C_4$-alkoxy, trifluoromethoxy, $C_1-C_4$-alkylthio, trifluoromethylthio, aminosulphonyl or $C_1-C_2$-alkoxycarbonyl], or $R^3$ and $R^4$ together represent $C_4-C_5$-alkanediyl, which is optionally interrupted by an oxygen bridge or by a bridge

wherein $R^5$ represents $C_1-C_3$-alkyl, $C_1-C_3$-alkylcarbonyl or phenyl [which is optionally substituted by fluorine, chlorine, bromine, cyano, nitro, $C_1-C_2$-alkyl, trifluoromethyl or $C_1-C_2$-alkoxy];

or in which, furthermore, $R^4$ represents the radical $-O-R^6$, wherein $R^6$ represents $C_1-C_8$-alkyl [which is optionally substituted by fluorine or chlorine], $C_3-C_6$-alkenyl, $C_1-C_3$-alkoxy-carbonyl-$C_1-C_2$-alkyl; phenyl, phenethyl or benzyl [which are optionally substituted by fluorine, chlorine, nitro, cyano, $C_1-C_2$-alkyl, $C_1-C_2$-alkoxy or $C_1-C_2$-alkoxycarbonyl], $C_5-C_6$-cycloalkyl or $C_5-C_6$-cycloalkyl-$C_1-C_2$-alkyl;

or in which, furthermore, $R^4$ represents the radical

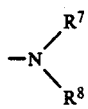

wherein $R^7$ represents hydrogen or methyl and $R^8$ represents $C_1-C_2$-alkyl [which is optionally substituted by fluorine, chlorine, cyano, $C_1-C_2$-alkoxy or $C_1-C_2$-alkoxy-carbonyl], $C_3-C_6$-cycloalkyl, phenethyl, benzyl or phenyl [which are optionally substituted by fluorine, chlorine, bromine, nitro, cyano, $C_1-C_2$-alkyl, $C_1-C_2$-alkoxy or $C_1-C_2$-alkoxy-carbonyl].

The invention furthermore preferably relates to 1:1 adducts of compounds of the formula (I)—as defined above, wherein M represents hydrogen—with hydrogen halide acids, such as hydrogen chloride, hydrogen bromide and hydrogen iodide, with sulphuric acid or trifluoroacetic acid, with alkanesulphonic acids which have up to 4 carbon atoms and are optionally substituted by fluorine or chlorine, or with benzene- or naphthalene-sulphonic acids, which are optionally substituted by fluorine, chlorine, bromine or methyl.

The invention particularly relates to compounds of the formula (I) in which

M represents hydrogen or one equivalent of sodium, potassium or calcium, $R^1$ represents difluoromethyl or trifluoromethyl, the radical $-O-R^1$ being in the ortho-position, $R^2$ represents hydrogen, $R^3$ represents the radical

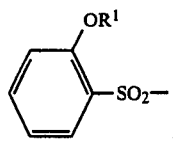

wherein $R^1$ represents difluoromethyl or trifluoromethyl, and $R^4$ represents the radical $-O-R^6$, wherein $R^6$ represents $C_1-C_4$-alkyl [which is optionally substituted by fluorine or chlorine], $C_3-C_5$-alkenyl, $C_1-C_2$-alkoxy-carbonylmethyl, phenyl, phenethyl or benzyl [which are optionally substituted by fluorine, chlorine, nitro, cyano, methyl, methoxy or methoxycarbonyl], cyclohexyl or cyclohexylmethyl, and—in the case where M represents hydrogen—the 1:1 adducts of the compounds defined above with hydrochloric acid, sulphuric acid, trifluoroacetic acid, methanesulphonic acid, benzenesulphonic acid and p-toluenesulphonic acid.

If, for example, 2-trifluoromethoxy-benzenesulphonyl chloride and N′-(4,6-dimethyl-pyrimidin-2-yl)-N″-allyloxyguanidine are used as starting substances for process variant (a), the course of the reaction can be outlined by the following equation:

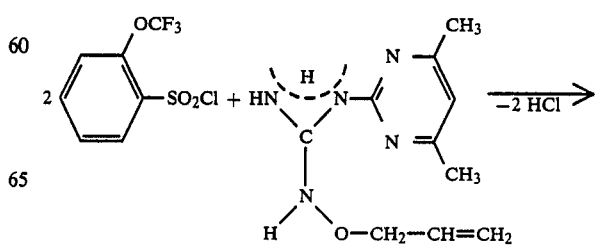

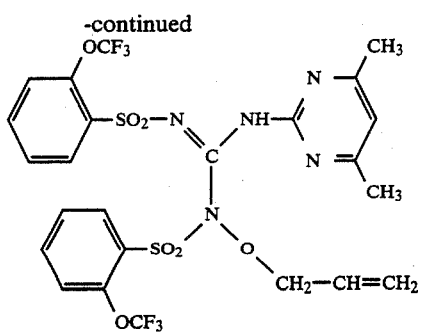
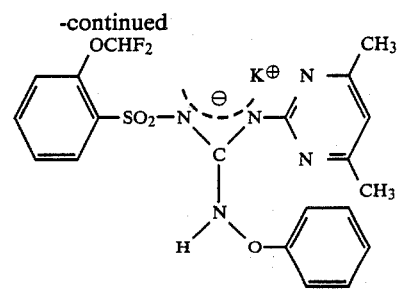

If, for example, N'-(4,6-dimethyl-pyrimidin-2-yl)-N''-methoxy-N'',N''''-bis-(2-chloro-4-trifluoromethoxybenzenesulphonyl)-guanidine and N,N-dimethylhydrazine are used as starting substances for process variant (b), the course of the reaction can be outlined by the following equation:

If, for example, N'-(4,6-dimethyl-pyrimidin-2-yl)-N''-ethoxy-N'',N''''-bis-(2-trifluoromethoxy-benzenesulphonyl)-guanidine and hydrochloric acid are used as starting substances for process variant (d), the course of the reaction can be outlined by the following equation:

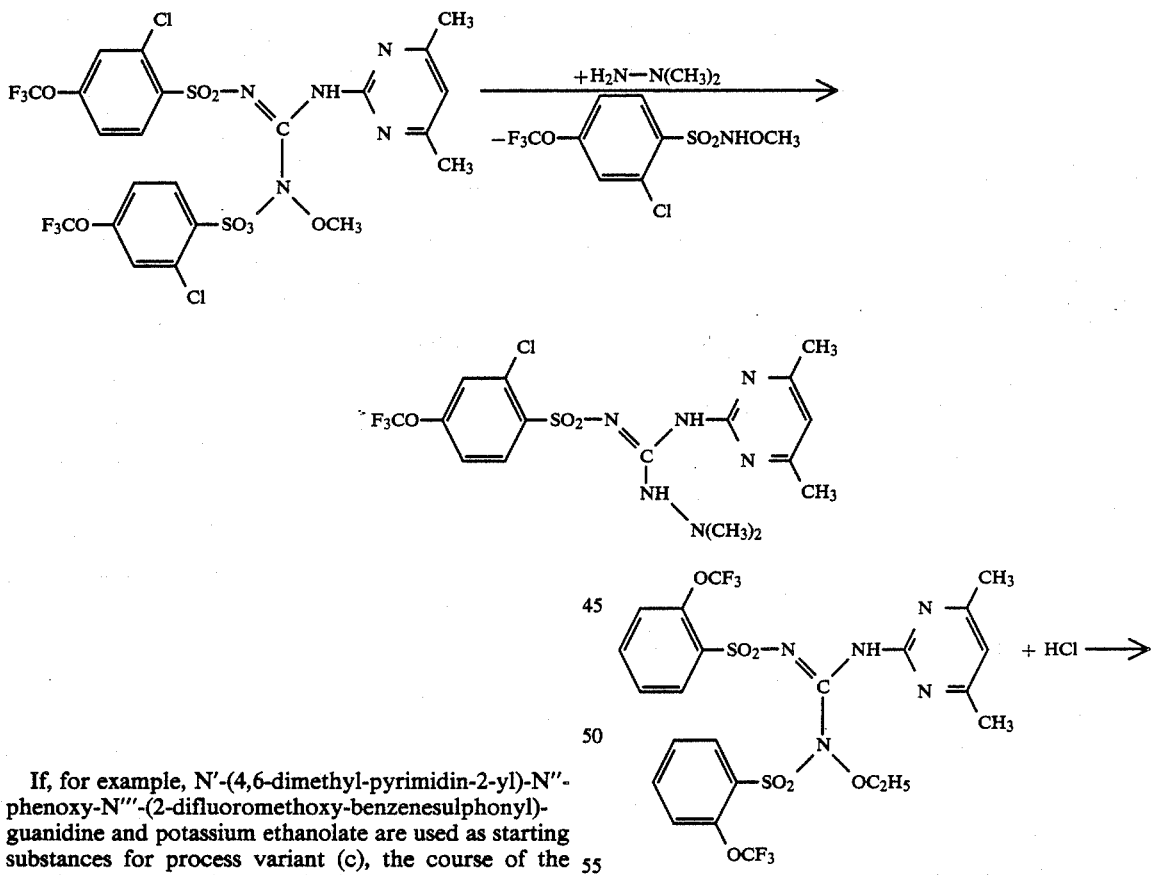

If, for example, N'-(4,6-dimethyl-pyrimidin-2-yl)-N''-phenoxy-N''''-(2-difluoromethoxy-benzenesulphonyl)-guanidine and potassium ethanolate are used as starting substances for process variant (c), the course of the reaction can be outlined by the following equation:

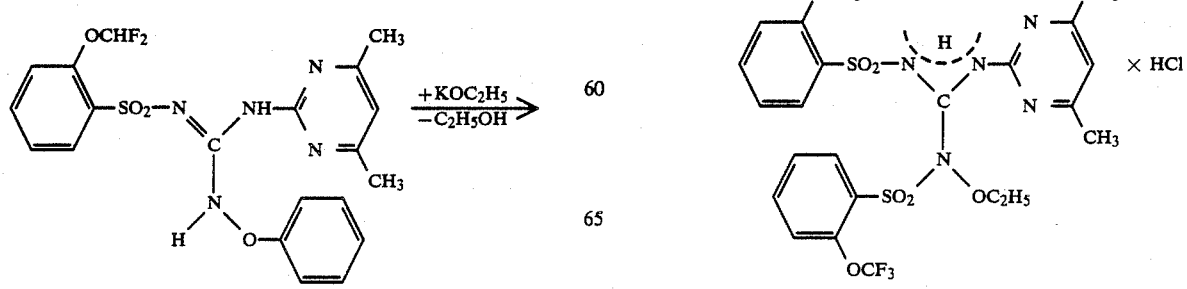

Formula (II) provides a general definition of the guanidine derivatives to be used as starting substances for process variant (a). In formula (II), $R^4$ preferably and particularly has the same meaning as is given above as preferred or as particularly preferred in the context of the definition of the substituents of the formula (I).

Examples which may be mentioned of starting substances of the formula (II) are: N'-(4,6-dimethyl-pyrimidin-2-yl)-N''-methoxy-guanidine, -N''-ethoxy-guanidine, -N''-propoxy-guanidine, -N''-isopropoxy-guanidine, -N''-butoxy-guanidine, -N''-isobutoxy-guanidine, -N''-sec.-butoxy-guanidine, -N''-pentoxy-guanidine, -N''-isopentoxy-guanidine, -N''-sec.-pentoxy-guanidine, -N''-hexyloxy-guanidine, -N''-isohexyloxy-guanidine, -N''-heptyloxy-guanidine, -N''-isoheptyloxy-guanidine, -N''-octyloxy-guanidine, -N''-isooctyloxy-guanidine, -N''-allyloxy-guanidine, -N''-crotyloxy-guanidine, -N''-(2-chloro-ethoxy)-guanidine, -N''-(2-fluoro-ethoxy)-guanidine, -N''-(2-chloro-propoxy)-guanidine, -N''-(3-chloro-propoxy)-guanidine, -N''-(4-chloro-butoxy)-guanidine, -N''-methoxycarbonylmethoxy-guanidine, -N''-ethoxycarbonylmethoxy-guanidine, -N''-(1-methoxycarbonyl-ethoxy)-guanidine, -N''-(1-ethoxycarbonyl-ethoxy)-guanidine, -N''-aminocarbonylmethoxy-guanidine, -N''-(phenyl-ethoxy)-guanidine, -N''-phenoxy-guanidine, -N''-(4-methyl-benzyloxy)-guanidine, -N''-(4-chloro-benzyloxy)-guanidine, -N''-(4-nitrobenzyloxy)-guanidine, -N''-(2,6-dichloro-benzyloxy)-guanidine, -N''(4-ethoxy-carbonyl-benzyloxy)-guanidine and -N''-(4-methoxycarbonyl-benzyloxy)-guanidine.

Some of the starting substances of the formula (II) are known (compare J. Chem. Soc. 1962, 3915); some of them are disclosed in application Ser. No. 578, 345, filed Feb. 9, 1984, now pending, corresponding to DE-OS (German Published Specification) No. 3,334,455; and No. EP-A-117 014.

The compounds of the formula (II) are obtained by a process in which 2-cyanoamino-4,6-dimethyl-pyrimidine of the formula (V)

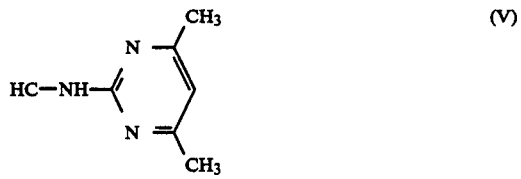

is reacted with amino compounds of the formula (VI)

in which $R^4$ has the abovementioned meaning, or with hydrochlorides thereof, if appropriate in the presence of diluents, such as, for example, ethanol, isopropanol or butanol, at temperatures between 20° C. and 150° C., preferably between 50° C. and 120° C., and, if appropriate, the reaction products are treated with acid acceptors, such as, for example, ammonia, sodium hydroxide solution or sodium carbonate.

2-Cyanoamino-4,6-dimethyl-pyrimidine of the formula (V) is already known (compare J. Chem. Soc. 1953, 1725).

The amino compounds of the formula (VI) are likewise already known, and can be prepared by processes which are known per se (compare Chem. Pharm. Bull. 15, (1967), 345; Bull. Soc. Chim. France 1958, 664; Synthesis 1976, 682; J. Chem. Soc. 1930, 228 and Helv. Chim. Acta 45 (1962), 1387).

Formula (III) provides a general definition of the fluoroalkoxybenzenesulphonic acid chlorides also to be used as starting substances for process (a). In formula (III), $R^1$ and $R^2$ preferably and particularly have the same meanings as are given above as preferred or as particularly preferred to the context of the definition of the substituents of the formula (I).

Examples which may be mentioned of starting substances of the formula (III) are: 2-difluoromethoxy- and 2-trifluoromethoxy-benzenesulphonyl chloride and 2-chloro-4-trifluoromethoxy-, 3-chloro-4-trifluoromethoxy- and 5-chloro-2-trifluoromethoxy-benzenesulphonyl chloride.

The fluoroalkoxybenzenesulphonic acid chlorides of the formula (III) are known and can be prepared by processes which are known per se (compare Zh. Org. Khim [J. Org. Chem. USSR] 8 (1972), 1023-1026 [English 1032-1034]; and EP-OS (European Published Specifications) Nos. 23,422, 44,808, 64,322 and 72,347).

Formula (ID) provides a general definition of the fluoroalkoxyphenylsulphonylguanidines to be used as starting substances for process variant (b). In formula (ID), $R^1$, $R^2$, and $R^4$ preferably and particularly have the same meanings as are given above as preferred or as particularly preferred in the context of the definition of the substituents of formula (I).

Examples which may be mentioned of compounds of the formula (ID): are N'-(4,6-dimethyl-pyrimidin-2-yl)-N''-methoxy-N'',N'''-bis-(2-difluoromethoxy-benzenesulphonyl)-guanidine and N'-(4,6-dimethyl-pyrimidin-2-yl)-N''-methoxy-N'',N'''-bis-(2-trifluoromethoxy-benzenesulphonyl)-guanidine.

The compounds of the formula (ID) can be prepared by the process described above under (a).

Formula (IV) provides a general definition of the amino compounds also to be used as starting substances in process variant (b). In formula (IV), $R^3$ and $R^4$ preferably and particularly have the same meanings as have been given above as preferred or as particularly preferred in the context of the definition of the substituents of formula (I).

Examples which may be mentioned of starting substances of the formula (IV) are: N,N-dimethylhydrazine, phenylhydrazine, O-methyl-hydroxylamine, O-ethyl-hydroxylamine and O-propyl-, O-isopropyl-, O-butyl-, O-isobutyl-, O-sec.-butyl-, O-pentyl-, O-isopentyl-, O-sec.-pentyl-, O-hexyl-, O-isohexyl-, O-heptyl-, O-isoheptyl-, O-octyl-, O-isooctyl-, O-allyl-, O-crotyl-, O-(2-chloro-ethyl)-, O-(2-fluoro-ethyl)-, O-(2-chloropropyl)-, O-(3-chloro-propyl)-, O-(4-chloro-butyl)-, O-methoxycarbonylmethyl-, O-ethoxycarbonylmethyl-, O-(1-methoxycarbonyl)-ethyl-, O-(1-ethoxycarbonyl)-ethyl-, O-aminocarbonylmethyl-, O-(2-phenyl-ethyl)-, O-phenyl-, O-(4-methyl-benzyl)-, O-(4-fluoro-benzyl)-, O-(4-chloro-benzyl)-, O-(4-nitro-benzyl)-, O-(2,6-dichloro-benzyl)-, O-(4-methoxycarbonyl-benzyl)- and O-(4-ethoxycarbonyl-benzyl)-hydroxylamine.

Amino compounds of the formula (IV) are known and can be prepared by processes which are known per se (compare Chem. Pharm. Bull. 15 (1967), 345; Bull. Soc. Chim. France 1958, 664; Synthesis 1976, 682; J. Chem. Soc. 1930, 228 and Helv. Chim. Acta 45 (1962), 1387).

Formula (I)—with the proviso that M represents hydrogen—provides a general definition of the fluoroalkoxyphenylsulphonylguanidines to be used as starting substances in process variant (c). In formula (I)—where this relates to the compounds to be used as starting substances for process (c)—M represents hydrogen and the radicals $R^1$, $R^2$, $R^3$ and $R^4$ preferably and particularly have the same meanings as are given above as preferred or as particularly preferred in the context of the definition of the substituents of the formula (I).

The compounds of the formula (I) to be used as starting substances for process (c) can be prepared by the process described under (a) and (b).

Examples which may be mentioned of the metal hydroxides, hydrides and alkanolates and organometallic compounds to be used in process (c) are: the hydroxides of lithium, sodium, potassium, magnesium and calcium, the hydrides of lithium, sodium and calcium, sodium methanolate and ethanolate, potassium methanolate and ethanolate and potassium tert.-butanolate, and butyl-lithium and isopropyl-magnesium chloride.

Formula (I)—with the proviso that M represents hydrogen—provides a general definition of the fluoroalkoxyphenylsulphonylguanidines to be used as starting substances in process variant (d). In formula (I)—where this relates to the compounds to be used as starting substances for process (d)—M represents hydrogen and the radicals $R^1$, $R^2$, $R^3$ and $R^4$ preferably and particularly have the same meanings as are given above as preferred or as particularly preferred in the context of the definition of the substituents for formula (I).

The compounds of the formula (I) to be used as starting substances for process (d) can be prepared by the processes described under (a) and (b).

Strong acids are employed as starting substances in process (d). These are preferably hydrogen halide acids, such as hydrogen chloride, hydrogen bromide or hydrogen iodide, and furthermore sulphuric acid or alkanesulphonic acids which have up to 4 carbon atoms and are optionally substituted by fluorine or chlorine, such as, for example, methanesulphonic acid, ethanesulphonic acid, chloromethanesulphonic acid, 2-chloroethanesulphonic acid and trifluoromethanesulphonic acid, trifluoroacetic acid, and furthermore benzenesulphonic acid, p-toluenesulphonic acid, naphthalene-1-sulphonic acid, naphthalene-2-sulphonic acid and naphthalene-1,4-, -1,5-, -1,6-, -2,6- and -2,7-disulphonic acid.

Process (a) according to the invention for the preparation of the new compounds of the formula (I) is preferably carried out using diluents. Possible diluents are virtually all the inert organic solvents, but preferably aprotic polar solvents. These include optionally substituted hydrocarbons, such as, for example, methylene chloride, chloroform, 1,2-dichloroethane, toluene, xylene and chlorobenzene, nitriles, such as, for example, acetonitrile and propionitrile, ethers, such as, for example, 1,2-dimethoxyethane, tetrahydrofuran and dioxane, and dimethylformamide, dimethylacetamide, dimethylsulphoxide, sulpholane, pyridine and 2-methyl-5-ethylpyridine.

Virtually all the acid-binding agents which are customarily used can be employed as acid acceptors in process (a). These include, in particular, alkali metal and alkaline earth metal hydroxides, alkali metal and alkaline earth metal hydrides, organometallic compounds, such as butyl-lithium, and furthermore aliphatic, aromatic or heterocyclic amines, such as trimethylamine, triethylamine, N,N-dimethylaniline, N,N-dimethyl-benzylamine, diazabicyclooctane (DABCO), diazabicyclononene (DBU), diazabicycloundecene (DBU), pyridine, 2-methyl-5-ethylpyridine and 4-dimethylaminopyridine.

The reaction temperatures can be varied within a substantial range in process (a). In general, the reaction is carried out between $-80°$ and $+100°$ C., preferably between $-30°$ and $+50°$ C. Process (a) according to the invention is in general carried out under normal pressure.

For carrying out process (a), in general between 2 and 5 moles, preferably between 2.1 and 3 moles, of fluoroalkoxybenzenesulphonic acid chloride of the formula (III) are employed per mole of guanidine derivative of the formula (II).

The reaction components are usually brought together at room temperature or with external cooling, and the reaction mixture is stirred until the reaction has ended.

The new compounds are worked up and isolated by customary methods: after distilling off volatile components, if appropriate, the mixture is shaken with water and a water-immiscible solvent, such as, for example, methylene chloride, chloroform or toluene, and the organic phase is washed with water, dried, filtered and concentrated. The products of the formula (I), which remain in the residue, are made to crystallize by digestion with organic solvents, such as, for example, diethyl ether, ethyl acetate, ethanol or isopropanol, and, if appropriate, purified by recrystallization.

Process (b) according to the invention is preferably carried out using diluents. Possible diluents are virtually all the inert organic solvents. These include, in particular, alcohols, such as methanol, ethanol and n- and i-propanol, ethers, such as tetrahydrofuran, dioxane and 1,2-dimethoxyethane, esters, such as methyl acetate and ethyl acetate, nitriles, such as, for example, acetonitrile or propionitrile, and dimethylformamide and water.

Acid-binding agents which do not noticeably compete with the amino compounds of the formula (IV) in their nucleophilic properties can be used as acid acceptors in process (b).

Acid acceptors of this type which may be mentioned are alkali metal and alkaline earth metal carbonates, such as, for example, potassium carbonate and calcium carbonate, tertiary amines, such as, for example, triethylamine, N,N-dimethylaniline and N,N-dimethylbenzylamine, and nitrogen-containing heterocyclic compounds, such as, for example, pyridine, diazabicyclooctane (DABCO) and diazabicycloundecene (DBU).

The reaction temperature can be varied within a substantial range in process (b). In general, the reaction is carried out between $0°$ C. and $150°$ C., preferably between $10°$ C. and $100°$ C. Process (b) is in general carried out under normal pressure.

For carrying out process (b) according to the invention, in general between 1 and 10 moles, preferably between 2 and 5 moles, of amino compound of the formula (IV) of hydrochloride thereof are employed per mole of compound of the formula (ID).

In general, the compound of the formula (ID) with the diluent at $20°$ C. or with gentle cooling, and the amino compound of the formula (IV) or the hydrochloride thereof and, if appropriate, a suitable acid acceptor are added. The reaction mixture is then in general stirred at room temperature or elevated temperature until the reaction has ended.

Working up can be effected by customary methods. If the products of the formula (I) are obtained from the reaction mixture as crystals, they can be isolated by filtration with suction. Otherwise—if appropriate after concentration—the mixture is diluted with water and extracted with a solvent which is virtually water-immiscible, such as, for example, methylene chloride. The products of the formula (I) can be obtained in a pure form by washing the extraction solution with water, drying, filtering, concentrating the filtrate and recrystallizing the residue.

Process (c) according to the invention is preferably carried out using diluents. Possible diluents are virtually all the inert organic solvents. These include, in particular, alcohols, such as, for example, ethanol and n- and iso-propanol, ethers, such as, for example, tetrahydrofuran, dioxane and 1,2-dimethoxyethane, esters, such as, for example, ethyl acetate and methyl acetate, and nitriles, such as, for example, acetonitrile.

The reaction temperature can be varied within a substantial range in process (c). In general, the reaction is carried out between $-20°$ C. and $+50°$ C., preferably between $0°$ C. and $30°$ C. Process (c) is in general carried out under normal pressure.

For carrying out process (c) according to the invention, in general between 0.9 and 1.2 moles, preferably between 0.95 and 1.1 moles, of metal compound are employed per mole of the compound of the formula (I).

In general, the compounds of the formula (I) and the diluent are taken and—if appropriate with gentle external cooling—the metal compound—if appropriate dissolved in the diluent—is metered in. The reaction mixture is stirred until the reaction has ended. The salt-like products of the formula (I) are in general obtained in the form of crystals and can be isolated by filtration with suction.

Process (d) is preferably carried out using diluents. Possible diluents are virtually all the inert organic solvents. These include, in particular, alcohols, such as methanol, ethanol and n- and iso-propanol, ethers, such as tetrahydrofuran, dioxane and 1,2-dimethoxyethane, esters, such as methyl acetate and ethyl acetate, and ketones, such as acetone, methyl ethyl ketone and methyl isobutyl ketone.

If the acids used as starting substances are employed in aqueous solution, it may also be advantageous to use acetic anhydride as the diluent.

The reaction temperature can be varied within a substantial range in process (d). In general, the reaction is carried out between $-20°$ C. and $+50°$ C., preferably between $0°$ C. and $30°$ C. Process (d) is in general carried out under normal pressure.

For carrying out process (d) according to the invention, in general between 1 and 10 moles, preferably 1 and 5 moles, of a strong acid are employed per mole of the compound of the formula (I).

In general, the compounds of the formula (I) and the diluent are taken and—if appropriate with gentle external cooling—the strong acid is metered in. The reaction mixture is stirred until the reaction has ended. The 1:1 adducts are in general obtained in the form of crystals and can be isolated by filtration with suction.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera:

Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopis, Papaver and Centaurea.

Dicotyledon cultures of the genera:

Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera:

Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera:

Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee planations, tea plantations, rubber plantations, oil palm plantations, cocoa plantations, soft fruit plantings and hopfields, and for the selective combating of weeds in annular cultures.

The active compounds according to the invention can be used for combating monocotyledon and dicotyledon weeds in monocotyledon and dicotyledon crops by the pre-emergence and post-emergence method.

Control of germinating, emerging and already established weeds in permanent crops is also possible using the active compounds according to the invention, as is total control of vegetation on non-agricultural land.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main:

aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Further additives can be mineral and vegetable oils.

It is possible to use colorants such as inorganic pigments, for example iron oxide, titanium oxide and Prussian blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, N-(2-benzothiazolyl)-N,N'-dimethyl-urea, 3-(3-chloro-4-methylphenyl)-1,1-dimethylurea, 3-(4-isopropylphenyl)-1,1-dimethylurea, 4-amino-6-(1,1-dimethylethyl)-3-methylthio-1,2,4-triazin-5(4H)-one, 4-amino-6-(1,1-dimethyl-ethyl)-3-ethylthio-1,2,4-triazin-5(4H)-one, 1-amino-6-ethylthio-3-(2,2-dimethylpropyl)-1,3,5-triazin-2,4-(1H,3H)-dione, 4-amino-3-methyl-6-phenyl-1,2,4-triazin-5(4H)-one, 2-chloro-4-ethylamino-6-isopropyl-amino-1,3,5-triazine, the R-enantiomer of (trimethylsilyl)-methyl 2-[4-(3,5-dichloro-pyridin-2-oxy)-phenoxy]-propionate, the R-enantiomer of (2-benzyloxy)-ethyl 2-[4-(3,5-dichloropyridyl-2-oxy)-phenoxy]-propionate, 2,4-dichlorophenoxyacetic acid, 2-(2,4-dichlorophenoxy)-propionic acid, 4-chloro-2-methyl-phenoxy-acetic acid, 2-(2-methyl-4-chloro-phenoxy)-propionic acid, 3,5-diiodo-4-hydroxy-benzonitrile, 3,5-dibromo-4-hydroxybenzonitrile and diphenyl ether and phenylpyridazines, such as, for example, pyridates. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. In the case of post-emergence treatment, the active compounds can also be applied in combination with emulsifiable oils, surface-active substances and other additives. They can also be incorporated into the soil before sowing.

The amount of active compound used can vary within a substantial range. It depends essentially on the nature of the desired effect. In general, the amounts used are between 0.001 and 10 kg of active compound per hectare of soil surface, preferably between 0.01 to 5 kg per ha.

Compounds of the formula (I) also exhibit a fungicidal action, for example against *Pyricularia oryzae* on rice.

The preparation and use of the active compounds according to the invention can be seen from the following examples.

PREPARATION EXAMPLES

Example 1

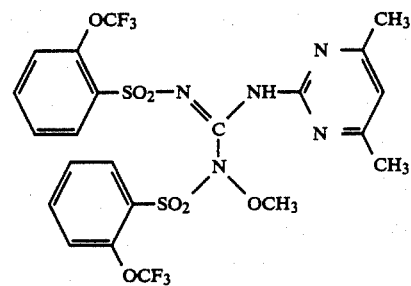

(Process (a))

31.3 g (0.12 mole) of 2-trifluoromethoxy-benzene-sulphonyl chloride are added in portions to a mixture, cooled to −10° C., of 9.8 g (0.05 mole) of N'-(4,6-dimethyl-pyrimidin-2-yl)-N''-methoxy-guanindine and 50 ml of pyridine, with stirring. The reaction mixture is stirred at −10° C. for one hour and at 20° C. for two hours. After concentrating under a waterpump vacuum, the residue is taken up in methylene chloride and this solution is washed with 5% strength hydrochloric acid and with water, dried, filtered and concentrated. The residue is made to crystallize by digestion with isopropanol.

14.5 g (45% of theory) of N'-(4,6-dimethyl-pyrimidin-2-yl)-N''-methoxy-N'',N''''-bis-(2-trifluoromethoxy-phenylsulphonyl)-guanidine of melting point 158° C. are obtained.

Example 2

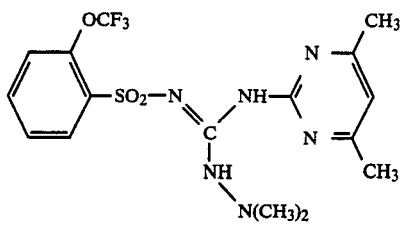

(Process (b))

1.5 g (0.025 mole) of N,N-dimethylhydrazine are added to a mixture of 6.4 g (0.01 mole) of N'-(4,6-dimethyl-pyrimidin-2-yl)-N''-methoxy-N'',N'''-bis-(2-trifluoromethoxy-phenylsulphonyl)-guanidine, 20 ml of ethanol and 10 ml of water. The reaction mixture is heated at the boiling point under reflux for one hour and, after cooling, is filtered. The product crystallizes out when the filtrate is left to stand for a prolonged period.

1.5 g (35% of theory) of N'-(4,6-dimethyl-pyrimidin-2-yl)-N''-dimethylamino-N'''-(2-trifluoromethoxy-phenylsulphonyl)-guanidine of melting point 170° C. are obtained.

Example 3

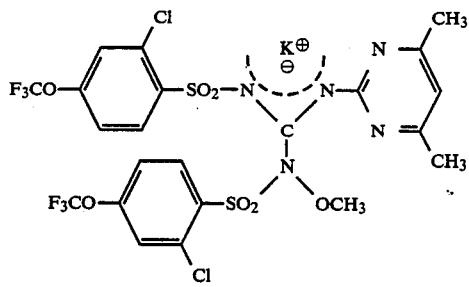

(Process (c))

A solution of 0.36 g (0.005 mole) of potassium methanolate in 15 ml of methanol is added to a mixture of 3.6 g (0.005 mole) of N'-(4,6-dimethyl-pyrimidine-2-yl)-N''-methoxy-N'',N'''-bis-(2-chloro-4-trifluoromethoxybenzenesulphonyl)-guanidine and 15 ml of acetone, and the mixture is stirred at 20° C. for two hours. The product, which precipitates as crystals, is isolated by filtration with suction. 1.8 g (55% of theory) of the potassium salt of N'-(4,6-dimethyl-pyrimidin-2-yl)-N''-methoxy-N'',N'''-bis-(2-chloro-4-trifluoromethoxy-benzenesulphonyl)-guanidine of melting point >300° C. are obtained.

Example 4

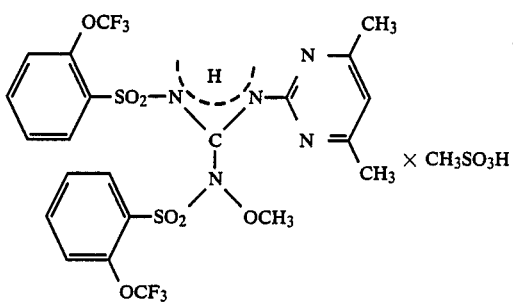

(Process (d))

A mixture of 6.4 g (0.01 mole) of N'-(4,6-dimethyl-pyrimidin-2-yl)-N''-methoxy-N'',N'''-bis-(2-trifluoromethoxy-phenylsulphonyl)-guanidine, 1.0 g (0.01 mole) of methanesulphonic acid and 50 ml of acetone is stirred at 20° C. for 12 hours and then concentrated. The residue is triturated with ligroin and filtered off with suction.

6.0 g (81% of theory) of the 1:1 adduct of N'-(4,6-dimethyl-pyrimidin-2-yl)-N''-methoxy-N'',N'''-bis-(2-trifluoromethoxy-phenylsulphonyl)-guanidine and methanesulphonic acid of melting point 134° C. are obtained.

The compounds of the formula (I) listed in the following table can be prepared by the processes described by way of example in the preceding examples:

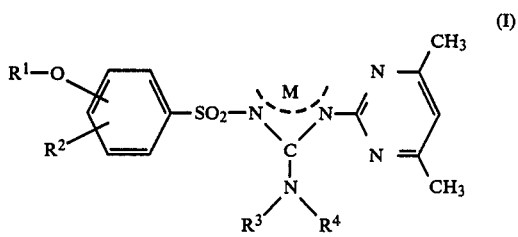

(I)

TABLE 1

| Example No. | $R^1$—O— | $R^2$ | $R^3$ | $R^4$ | M | Melting point (°C.) |
|---|---|---|---|---|---|---|
| 5 | 2-OCH$_2$F | H | OCHF$_2$ / SO$_2$— | —OCH$_3$ | H | 163 |
| 6 | 2-OCF$_3$ | H | H | —OCH$_3$ | H | 128 |
| 7 | 4-OCF$_3$ | 2-Cl | Cl, F$_3$CO—, SO$_2$— | —OCH$_3$ | H | 141-143 |

TABLE 1-continued

| Example No. | R¹—O— | R² | R³ | R⁴ | M | Melting point (°C.) |
|---|---|---|---|---|---|---|
| 8 | 4-OCF₃ | 3-Cl | 3-Cl,4-F₃CO-C₆H₃-SO₂— | —OCH₃ | H | viscous oil |
| 9 | 2-OCF₃ | 5-Cl | 5-Cl,2-F₃CO-C₆H₃-SO₂— | —OCH₃ | H | 140 (decomposition) |
| 10 | 2-OCF₃ | H | 2-F₃CO-C₆H₄-SO₂— | —OC₂H₅ | H | 163 |
| 11 | 2-OCF₃ | H | 2-F₃CO-C₆H₄-SO₂— | —OCH₂C(=O)OC₂H₅ | H | 147 |
| 12 | 2-OCF₃ | H | 2-F₃CO-C₆H₄-SO₂— | —OCH₂-C₆H₅ | H | 173 |
| 13 | 2-OCHF₂ | H | 2-F₂HCO-C₆H₄-SO₂— | —OC₂H₅ | H | 159–160 |
| 14 | 2-OCHF₂ | H | 2-F₂HCO-C₆H₄-SO₂— | —OCH₂—CH=CH₂ | H | |
| 15 | 2-OCHF₂ | H | 2-F₂HCO-C₆H₄-SO₂— | —OCH₂CH₂-C₆H₅ | H | |
| 16 | 2-OCHF₂ | H | 2-F₂HCO-C₆H₄-SO₂— | —O-C₆H₅ | H | |
| 17 | 2-OCHF₂ | H | H | —OCH₃ | H | 138 |
| 18 | 2-OCHF₂ | H | H | —N(CH₃)₂ | H | 153 |
| 19 | 2-OCF₃ | H | H | —OCH₂COOC₂H₅ | H | |
| 20 | 2-OCF₃ | H | H | —OCH₂-C₆H₅ | H | |
| 21 | 4-OCF₃ | 2-Cl | H | —OCH₃ | H | 135 |
| 22 | 2-OCF₃ | H | H | —OC₂H₅ | H | 115 |

TABLE 1-continued

| Example No. | R¹—O— | R² | R³ | R⁴ | M | Melting point (°C.) |
|---|---|---|---|---|---|---|
| 23 | 2-OCHF₂ | H | H | —OC₂H₅ | H | 136 |
| 24 | 2-OCHF₂ | H | H | —OCH₂—C₆H₅ | H | 242 (decomposition) |
| 25 | 2-OCHF₂ | H | 2-OCHF₂-C₆H₄-SO₂— | —OCH₂—C₆H₅ | H | 178 |
| 26 | 2-OCF₃ | H | 2-OCF₃-C₆H₄-SO₂— | H | H | 202 |
| 27 | 2-OCF₃ | H | 2-OCF₃-C₆H₄-SO₂— | —OC₃H₇—n | H | 151 |
| 28 | 2-OCHF₂ | H | 2-OCHF₂-C₆H₄-SO₂— | —OC₃H₇—n | H | 164 |
| 29 | 2-OCF₃ | H | CH₃ | —CH₃ | H | 150 |
| 30 | 2-OCF₃ | H | H | —CH₃ | H | 99 |
| 31 | 2-OCF₃ | H | 2-OCF₃-C₆H₄-SO₂— | —CH₃ | H | 190 |

TABLE 1a

| Example No. | 1:1 adducts of compounds of the formula (I) | melting point (°C.) |
|---|---|---|
| 7a | H₂SO₄-salt of example 7 | |
| 9a | H₂SO₄-salt of example 9 | |
| 10a | CH₃SO₃H-salt of example 10 | 124 |
| 12a | CH₃SO₃H-salt of example 12 | 143 (decomposition) |
| 13a | CH₃SO₃H-salt of example 13 | 65–70 |
| 27a | CH₃SO₃H-salt of example 27 | 80 (decomposition) |

PREPARATION OF STARTING SUBSTANCES OF THE FORMULA (II)

Example (II-1)

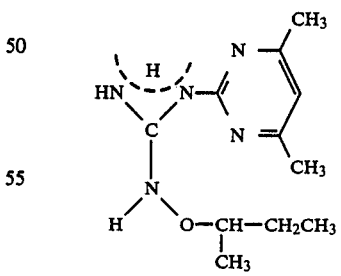

A mixture of 143 g (0.97 mole) of 2-cyanoamino-4,6-dimethyl-pyrimidine, 94.3 g (1.06 moles) of O-sec.-butyl-hydroxylamine and 190 ml of ethanol is heated at the boiling point under reflux for 6 hours. The mixture is then filtered with suction, the filtrate is concentrated and 500 ml of water are added to the residue. The product thereby obtained as crystals is isolated by filtration with suction.

131 g (57% of theory) of N'-(4,6-dimethyl-pyrimidin-2-yl)-N''-1-(1methyl-propoxy)-guanidine of melting point 78° C. are obtained.

Example (II-2)

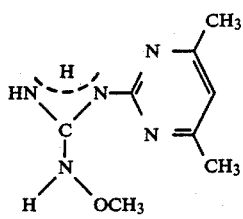

A mixture of 109 g (0.67 mole) of O-methylhyroxylamine hydrochloride, 99 g (0.67 mole) of 2-cyanoamino-4,6-dimethyl-pyrimidine and 600 ml of ethanol is heated at the boiling point under reflux for 7 hours. The alcohol is then distilled off under a waterpump vacuum, the residue is dissolved in hot water and this solution is added to 100 ml of concentrated ammonia. The product which has crystallised out is filtered off with suction and recrystallized from ethanol.

71.8 g (55% of theory) of N'-(4,6-dimethyl-pyrimidin-2-yl)-N''-methoxy-guanidine of melting point 134° C. to 136° C. are obtained.

The compounds of the formula (II) listed in the following table can be prepared analogously:

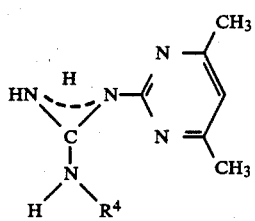

(II)

TABLE 2

| Example No. | $R^4$ | Melting point (°C.) |
|---|---|---|
| II-3 | $-OCH_2CH(CH_3)_2$ | 52 |
| II-4 | $-OCH_2CH=CH_2$ | 103 |
| II-5 | $-OCH(CH_3)_2$ | 84 |
| II-6 | $-OCH_2CH_2-\phi$ | |
| II-7 | $-OC_4H_9-n$ | Oil |
| II-8 | $-OC_8H_{17}-n$ | 58 |
| II-9 | $-O-CH_2CH_2CH_2Cl$ | 137 |
| II-10 | $-O-\phi$ | 192 (decomposition) |
| II-11 | $-OCH_2-COOCH_3$ | 148–149 |
| II-12 | $-OCH_2-COOC_2H_5$ | 98–99 |
| II-13 | $-OCH(CH_3)-COOCH_3$ | 147–148 |
| II-14 | $-OCH_2-\phi-CH_3$ | 85–86 |

TABLE 2-continued

| Example No. | $R^4$ | Melting point (°C.) |
|---|---|---|
| II-15 | $-OCH_2-\phi-F$ | 114–116 |
| II-16 | $-O-\phi(H)$ | |
| II-17 | $-OCH_2-\phi(H)$ | |
| II-18 | $-OCH_2CON(CH_3)_2$ | |
| II-19 | $-OCH_2OCH_3$ | |
| II-20 | $-OCH_2SCH_3$ | |
| II-21 | $-OCH_2-\phi-COOC_2H_5$ | 138 |
| II-22 | $-OCH_2CF_3$ | |
| II-23 | $-OCH_2-\phi(Cl,Cl)$ | 145 |
| II-24 | $-OCH_2-\phi-NO_2$ | 170–172 |
| II-25 | $-CH_2CH_2CH_3$ | 54 |
| II-26 | $-OCH_2COOC_3H_7-i$ | 112 |
| II-27 | $-OC_2H_5$ | 88 |
| II-28 | $-OCH_2-\phi$ | 102 |
| II-29 | $-OCH_2-\phi-Cl$ | 102–103 |

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, the active compounds according to the invention exhibit a very good herbicidal activity: especially the compounds of preparation Examples (1), (2), (4), (5) and (6).

EXAMPLE B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated emount of emulsifier is added and the concentrate is diluted with water to the desired concentration.

Test plants which have a height of 5–15 cm are sprayed with the precipitation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0%=no action (like untreated control)
100%=total destruction

In this test, the active compounds according to the invention exhibit a very good herbicidal activity: especially the compounds of preparation Examples (1), (2), (4), (5) and (6).

It will be understood that the specification and examples are illustrative but not limitative of the present invention and that other embodiments within the spirit and scope of the invention will suggest themselves to those skilled in the art.

We claim:

1. A fluoroalkoxyphenylsulphonylguanidine of the formula

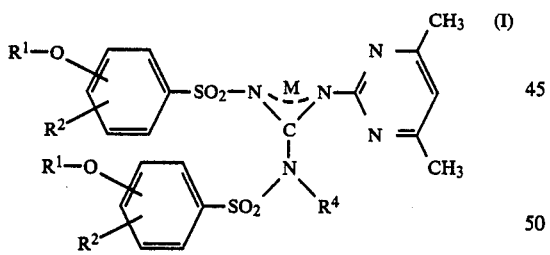

in which
M represents hydrogen or one equivalent of a metal,
$R^1$ represents $C_1$–$C_4$- fluoroalkyl, which optionally is chloro substituted,
$R^2$ represents hydrogen or halogen,
$R^4$ represents hydrogen, $C_1$–$C_6$-alkyl (which is optionally substituted by fluorine, chlorine, bromine, cyano, carboxyl, $C_1$–$C_4$-alkoxycarbonyl, hydroxyl or $C_1$–$C_4$-alkoxy), $C_3$–$C_6$-cycloalkyl, $C_3$–$C_6$-alkenyl, $C_3$–$C_6$-alkinyl, phenethyl or benzyl (which is optionally substituted by fluorine, chlorine, nitro, cyano, $C_1$–$C_4$-alkyl, $C_1$–$C_4$-alkoxy or $C_1$–$C_4$-alkoxy-carbonyl) or phenyl (which is optionally substituted by fluorine, chlorine, bromine, hydroxyl, cyano, nitro, amino, $C_1$–$C_4$-alkyl, trifluoromethyl, C–$C_4$-alkoxy, trifluoromethoxy, $C_1$–$C_4$-alkylthio, trifluoromethylthio, aminosulphonyl or $C_1$–$C_4$-alkoxy-carbonyl), or
$R^4$ represents the radical —O—$R^6$
wherein
$R^6$ represents $C_1$–$C_8$-alkyl (which is optionally substituted by fluorine, chlorine, $C_1$–$C_4$-alkoxy, $C_1$–$C_4$-alkylthio, $C_1$–$C_4$-alkylsulphinyl or $C_1$–$C_4$-alkylsulphonyl), $C_3$–$C_6$-alkenyl, $C_1$–$C_4$-alkoxy-carbonyl-$C_1$–$C_2$-alkyl, aminocarbonylmethyl, $C_1$–$C_4$-alkylamino-carbonyl-methyl, di($C_1$–$C_4$-alkyl)-amino-carbonyl-methyl; phenyl, phenethyl or benzyl (which are optionally substituted by fluorine, chlorine, nitro, cyano, $C_1$–$C_4$-alkyl, $C_1$–$C_4$-alkoxy or $C_1$–$C_4$-alkoxy-carbonyl), $C_3$–$C_6$-cycloalkyl or $C_3$–$C_6$-cycloalkyl-$C_1C_4$-alkyl;
or in which, furthermore,
$R^4$ represents the radical

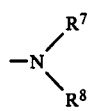

wherein
$R^7$ represents hydrogen or $C_1$–$C_4$-alkyl and
$R^8$ represents $C_1$–$C_4$-alkyl (which is optionally substituted by fluorine, chlorine, bromine, cyano, $C_1$–$C_4$-alkoxy or $C_1$–$C_4$-alkoxy-carbonyl, $C_3$–$C_6$-cycloalkyl, phenethyl, benzyl or phenyl (which are optionally substituted by fluorine, chlorine, bromine, nitro, cyano, $C_1$–$C_4$-alkyl, $C_1$–$C_4$-alkoxy or $C_1$–$C_4$-alkoxy-carbonyl), or a 1:1 adduct thereof with a strong acid.

2. A fluoralkoxyphenylsulphonylguanidine or adduct according to claim 1, in which
M represents hydrogen or one equivalent of sodium, potassium or calcium,
$R^1$ represents $C_1$–$C_2$-alkyl, which contains at least two fluorine substituents and optionally also one chlorine substituent,
$R^2$ represents hydrogen or chlorine,
$R^4$ represents hydrogen, $C_1$–$C_4$-alkyl (which is optionally substituted by fluorine, chlorine, bromine, cyano, carboxyl, $C_1$–$C_3$-alkoxycarbonyl, hydroxyl or $C_1$–$C_2$-alkoxy), $C_3$–$C_6$-cycloalkyl, $C_3$–$C_6$-alkenyl, $C_3$–$C_6$-alkinyl, phenethyl or benzyl (which is optionally substituted by fluorine, chlorine, nitro, cyano, $C_1$–$C_2$-alkyl, $C_1$–$C_2$-alkoxy or $C_1$–$C_2$-alkoxycarbonyl) or phenyl (which is optionally substituted by fluorine, chlorine, bromine, hydroxyl, cyano, nitro, amino, $C_1$–$C_4$-alkyl, trifluoromethyl, $C_1$–$C_4$-alkkoxy, trifluoromethoxy, $C_1$–$C_4$-alkylthio, trifluoromethylthio, aminosulphonyl or $C_1$–$C_2$-alkoxycarbonyl), or
$R^4$ represents the radical —O—$R^6$,
wherein
$R^6$ represents $C_1$–$C_8$-alkyl (which is optionally substituted by fluorine or chlorine), $C_3$–$C_6$-alkenyl, $C_1$–$C_3$-alkoxy-carbonyl-$C_1$–$C_2$-alkyl; phenyl, phenethyl or benzyl (which are optionally substituted by fluorine, chlorine, nitro, cyano, $C_1$–$C_2$-alkyl, $C_1$–$C_2$-alkoxy or $C_1$–$C_2$-alkoxycarbonyl), $C_5$–$C_6$-cycloalkyl or $C_5$–$C_6$-cycloalkyl-$C_1$–$C_2$-alkyl;
or in which, furthermore,
$R^4$ represents the radical

wherein

R⁷ represents hydrogen or methyl and

R⁸ represents $C_1-C_2$-alkyl (which is optionally substituted by fluorine, chlorine, cyano, $C_1-C_2$-alkoxy or $C_1-C_2$-alkoxy-carbonyl), $C_3-C_6$-cycloalkyl, phenethyl, benzyl or phenyl (which are optionally substituted by fluorine, chlorine, bromine, nitro, cyano, $C_1-C_2$-alkyl, $C_1-C_2$-alkoxy or $C_1-C_2$-alkoxycarbonyl).

3. A fluoralkoxyphenylsulphonylguanidine according to claim 1, in which

M represents hydrogen or one equivalent of sodium, potassium or calcium, $R^1$ represents difluoromethyl or trifluoromethyl, the radical —O—$R^1$ being in the ortho-position, $R^2$ represents hydrogen, $R^4$ represents the radical —O—$R^6$, wherein $R^6$ represents $C_1-C_4$-alkyl (which is optionally substituted by fluorine or chlorine), $C_3-C_5$-alkenyl, $C_1-C_2$-alkoxy-carbonylmethyl, phenyl, phenethyl or benzyl (which is optionally substituted by fluorine, chlorine, nitro, cyano, methyl, methoxy or methoxycarbonyl), cyclohexyl or cyclohexylmethyl, or—in the case where M represents hydrogen—a 1:1 adduct thereof with hydrochloric acid, sulphuric acid, trifluoroacetic acid, methanesulphonic acid, benzenesulphonic acid or p-toluenesulphonic acid.

4. A compound according to claim 1, wherein such compound is N'-(4,6-dimethyl-pyrimidin-2-yl)-N''-methoxy-N''', N''''-bis-(2-trifluoromethoxyphenylsulphonyl)-guanidine of the formula

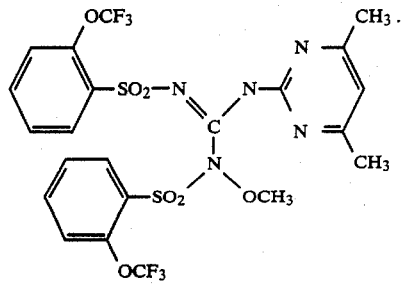

5. A compound according to claim 1, wherein such compound is N'-(4,6-dimethyl-pyrimidin-2-yl)-N''-methoxy-N''',N''''-bis(2-fluoromethoxyphenylsulphonyl)-guanidine of the formula

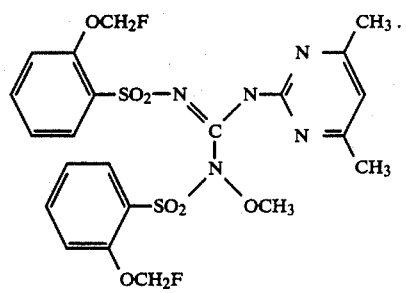

6. A herbicidal composition comprising a herbicidally effective amount of a compound or adduct according to claim 1 in admixture with a diluent.

7. A method of combating unwanted vegetation which comprises applying to such vegetation or a locus from which it is desired to exclude such vegetation a herbicidally effective amount of a compound or adduct according to claim 1.

8. The method according to claim 7 wherein such compound is

N'-(4,6-dimethyl-pyrimidin-2-yl)-N''-methoxy-N''', N''''-bis-(2-trifluoromethoxyphenylsulphonyl)-guanidine, N'-(4,6-dimethyl-pyrimidin-2-yl)-N''-methoxy-N''',N''''-bis(2-fluoromethoxyphenylsulphonyl)-guanidine, or a 1:1 adduct thereof with a strong acid.

* * * * *

UNITED STATES PATENT AND TRADEMARK OFFICE
CERTIFICATE OF CORRECTION

PATENT NO. : 4,725,304

DATED : February 16, 1988

INVENTOR(S) : Hans-Joachim Diehr, et al.

It is certified that error appears in the above-identified patent and that said Letters Patent is hereby corrected as shown below:

Col. 4, line 65 — End of line delete "for"

Col. 5, line 11 — Delete bonding lines in formula and substitute -- ◯ --

Col. 7, line 28 — Middle of formula delete " $\rangle\!-\!SO_3$ " and substitute: $\rangle\!-\!SO_2$ --

Col. 11, line 13 — Delete "process and substitute --processes--

Col. 14, line 13 — Correct spelling of --Galeopsis--

Col. 22, line 60 — After "cyanoamino" insert -- - --

Col. 23, line 2 — Before "methyl" insert -- - --

Col. 25, line 17 — Delete "precipitation" and substitute --preparation--

Col. 26, line 54 — Correct spelling of --alkoxy--

Col. 28, line 5 — Middle of formula delete " $\rangle C\!-\!N-$ " and substitute -- $\rangle C\!-\!NH-$ --

Signed and Sealed this

Sixth Day of September, 1988

Attest:

DONALD J. QUIGG

*Attesting Officer*   *Commissioner of Patents and Trademarks*